United States Patent [19]

Honda et al.

[11] 3,989,654

[45] Nov. 2, 1976

[54] PROCESS FOR PREPARING CIS-CHRYSANTHEMIC ACID

[75] Inventors: Toshiko Honda, Osaka; Nobushige Itaya; Akio Higo, both of Nishinomiya; Fukashi Horiuchi, Kawanishi, all of Japan

[73] Assignee: Sumitomo Chemical Company, Limited, Osaka, Japan

[22] Filed: Aug. 23, 1974

[21] Appl. No.: 500,018

[30] Foreign Application Priority Data

Nov. 22, 1973 Japan................................ 48-131988
Nov. 30, 1973 Japan................................ 48-135976

[52] U.S. Cl. ..................... 260/514 H; 260/343.2 R; 260/465 H
[51] Int. Cl.$^2$......................................... C07C 61/04
[58] Field of Search ................................. 260/514 H

[56] References Cited
UNITED STATES PATENTS

| | | | |
|---|---|---|---|
| 3,786,070 | 1/1974 | Martel et al. ................... | 260/514 H |
| 3,836,568 | 9/1974 | Higo et al. ..................... | 260/514 H |

Primary Examiner—Jane S. Myers
Attorney, Agent, or Firm—Stevens, Davis, Miller & Mosher

[57] ABSTRACT

A novel process for preparing cis-chrysanthemic acid comprising (1) hydrolysis of trans-δ-halogenodihydrochrysanthemic acid or ester thereof under neutrally kept condition with an alkaline earth metal carbonate, (2) conversion of the obtained trans-δ-hydroxydihydrochrysanthemic acid ester into a mixture of cis-chrysanthemic acid and iso-cis-chrysanthemic acid by reacting with a strong base, and (3) separation of the cis-chrysanthemic acid from the mixture by selective conversion of the iso-cis-chrysanthemic acid with water in the presence of an acid catalyst into cis-dihydrochrysanthemolactone, followed by separation of the cis-chrysanthemic acid from the lactone with a caustic alkali and an acid.

The present process is very useful for converting (−)-trans-chrysanthemic acid which is obtained, as a main remainder of racemic chrysanthemic acid prepared industrially, after (+)-trans-chrysanthemic acid was used for preparation of (+)-trans-chrysanthemic acid ester having a high insecticidal activity, into (+)-cis-chrysanthemic acid which is industrially valuable for preparation of insecticides.

1 Claim, No Drawings

PROCESS FOR PREPARING CIS-CHRYSANTHEMIC ACID

BACKGROUND OF THE INVENTION

The present invention relates to a new process for preparing cis-chrysanthemic acid comprising hydrolysis of trans-δ-halogenodihydrochrysanthemic acid or ester thereof (Step I), conversion of trans-δ-hydroxydihydrochrysanthemic acid ester to cis-chrysanthemic acid and iso-cis-chrysanthemic acid (Step II), and separation of cis-chrysanthemic acid from the mixture by selective conversion of iso-cis-chrysanthemic acid to cis-dihydrochrysanthemolactone.

SUMMARY OF THE INVENTION

An object of the present invention is to provide an industrially advantageous process for producing cis-chrysanthemic acid of the formula (I),

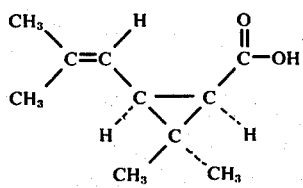

The present invention provides processes for preparing cis-crysanthemic acid of the formula (I), comprising Step I: hydrolyzing trans-δ-halogenodihydrochrysanthemic acid of the formula (VIII) or ester thereof of the formula (VI) under kept neutral condition by an alkaline earth metal carbonate to obtain trans-δ-hydroxy chrysanthemic acid of the formula (VII) or its ester of the formula (V), and further esterifying the acid with lower alkyl alcohol in the presence of mineral acid at about room temperature, Step II: reacting the obtained trans-δ-hydroxydihydrochrysanthemic acid ester of the formula (V) with more than equimolar amount of a strong base selected from the group consisting of alkali metal alkoxide, alkali metal hydride, alkali metal amide and alkali metal in the presence or absence of an inert solvent at a temperature of 100° to 200° C to obtain a mixture of cis-chrysanthemic acid of the formula (I) and iso-cis-chrysanthemic acid of the formula (III), and Step III: treating the obtained mixture of cis-chrysanthemic acid of the formula (I) and iso-cis-chrysanthemic acid of the formula (III) in the presence of an acid catalyst, in the presence or absence of an inert solvent, to convert selectively iso-cis-chrysanthemic acid to cis-dihydrochrysanthemolactone of the formula (II) and obtaining cis-chrysanthemic acid of the formula (I) from the mixture by separating the acid part from the neutral part by adding caustic alkali to the resulting mixture and removing the lactone in the neutral part according to the ordinary method.

Above mentioned steps are shown by the following reaction schema;

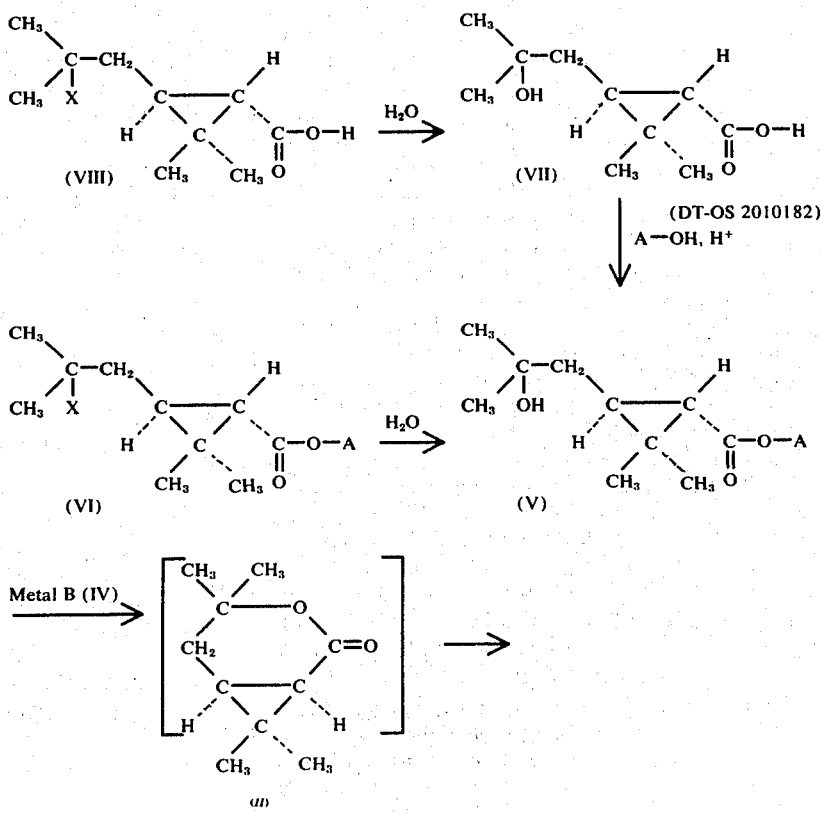

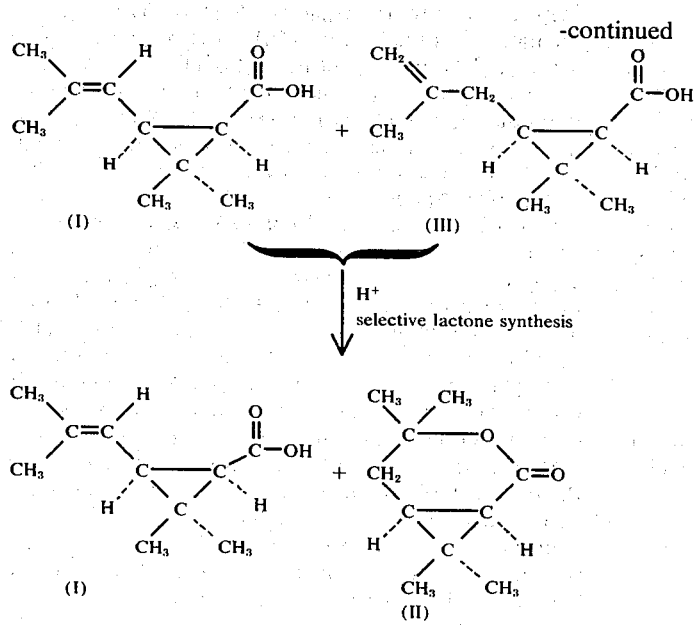

(wherein A represents $C_1$–$C_4$ alkyl or benzyl, Metal represents an alkali metal atom, Metal B of the formula (IV) represents alkali metal alkoxide, alkali metal hydride, alkali metal amide or alkali metal, and B represents a combination partner).

Various synthetic pyrethroid-type compounds derived from natural pyrethroids have various advantages such as immediate onset of action, high insecticidal activities and overall low toxicity to warm-blooded animals, and have been considered important as insecticides in the agricultural and sanitary fields. These compounds are esters having cyclopropanecarboxylic acid named chrysanthemic acid in their acid moiety.

It is known that (+)-trans-chrysanthemic acid (1-R-3-R-2,2-dimethyl-3-(2'-methyl-1'-propenyl)-cyclopropanecarboxylic acid) esters, included in natural pyrethrin as an active ingredient, have strong killing effect to injurious insects, and, however, it is also known that (+)-cis-chrysanthemic acid (1-R-3-S-2,2-dimethyl-3-(2'-methyl-1'-propenyl)-cyclopropanecarboxylic acid) esters have strong insecticidal activities by selecting types of composition (e.g. heating fumigant) and species of injurious insects (e.g. mosquitoes). The insecticidal activity of (+)-cis-chrysanthemic acid esters is shown in Reference example 5.

Typical examples of an alcohol moiety of these cis-chrysanthemic acid esters are shown as follows:
5-Benzyl-3-furylmethyl alcohol
3-Phenoxybenzyl alcohol
2-Allyl-3-methyl-4-hydroxy-2-cyclopentene-1-one
3,4,5,6-Tetrahydrophthalimidomethylol The main object of the present invention is to provide a method for converting (−)-trans-chrysanthemic acid, which is a main remainder of a racemic chrysanthemic acid prepared industrially after (+)-trans-chrysanthemic acid was used to prepare (+)-trans-chrysanthemic acid ester with higher insecticidal activity, to industrially valuable (+)-cis-chrysanthemic acid.

trans-δ-Halogenodihydrochrysanthemic acid, such as trans-δ-chlorodihydrochrysanthemic acid, used in Step I according to the present invention can be prepared easily by the method described in J. Chem. Soc., 1963 4957 (L. Crombie et al.), that is, by heating trans-chrysanthemic acid and conc.-hydrochloric acid.

And the process for preparing trans-δ-hydroxydihydrochrypanthemic acid, an intermediate of the present invention, was described in J. Sci. Food Arg. 3, 230 (1952) (S. H. Harper & R. A. Thompson), but the present inventors' reexamination of that latter process showed that as is clear from the Reference example 1, the process required considerably much amount of water and did not give good conversion ratio to the aimed compound. So it cannot be thought that the process is usable as an industrial method. And as is clear from the reference example 2, it became clear that hydration of trans-chrysanthemic acid or ester thereof was an equilibrium reaction, and further, as is clear from the Reference example 3, it was confirmed that the process did not give rise to the increase of volume efficiency per solvent employed by adding much amount of trans-crysanthemic acid.

Furthermore it is reported in J. Chem. Soc., 1963 4957 (L. Crombie et al.) that (±)-trans-δ-hydroxydihydrochrysanthemic acid was prepared by reacting (±)-trans-δ-chlorodihydrochrysanthemic acid with sodium hydroxide aqueous solution, but as is clear from the Reference example 4, the present inventors' reexamination of that reaction using the same reaction conditions proved that (±)-trans-chrysanthemic acid (dehydrogen chloride compound) was obtained as by-products.

According to the above-mentioned result it became clear that the Crombie's reaction was regulated by the amount of sodium hydroxide, the amount of water and the reaction temperature, and was low in reproducibility.

By studying an industrially advantageous preparation of trans-δ-hydroxychrysanthemic acid or ester thereof, a method has been found in which the hydroxy acid or the ester could be easily obtained in a high yield by reacting trans-crysanthemic acid with hydrogen halide in the presence or absence of an inert organic solvent and further hydrolyzing the obtained trans-δ-halogenodihydrochrysanthemic acid or ester thereof, which can be directly used in the next process without isolation by removing excess hydrogen halide with water, with alkaline earth metal carbonate (e.g. calcium carbonate, magnesium carbonate) as de-hydrogen halide agent in water with heating to proceed the reaction smoothly, to obtain the objective trans-δ-hydroxydihydrochrysanthemic acid or ester thereof having 60 to 70% of conversion ratio.

Yield of trans-δ-hydroxydihydrochrysanthemic acid is quantitative since the trans-chrysanthemic acid is recovered as by-product.

Though the above-mentioned reaction is two-step reaction, it can be regarded as one-step reaction since the obtained trans-δ-halogenodihydrochrysanthemic acid can be used for further reaction step without isolation.

The preparation of Step I according to the present invention will be illustrated in greater detail as follows.

As hydrogen halide used for the hydrogen halide addition reaction to trans-chrysanthemic acid, hydrogen chloride and hydrogen bromide are suitable, and preferably hydrogen chloride is used for an industrial process. And examples of the solvent used for the hydrogen halide addition reaction, that is, inert solvents not reacted with hydrogen halide, are exemplified by the hydrocarbon solvent (e.g. hexane, toluene), the halogenated hydrocarbon solvent (e.g. chloroform, carbontetrachloride), the ether type solvent, the ester type solvent, the organic acid type solvent and the ketone type solvent.

In case the alcohol type solvents are used, the objective compounds are obtained as the ester of the alcohol employed, and further the yield of the ester can be increased when a dehydrating agent such as thionyl chloride is used.

After excess of unreacted hydrogen halide in the reaction mixture was removed by washing with water, the obtained trans-δ-halogenodihydrochrysanthemic acid or ester thereof can be directly employed for the next hydrolysing step. At the hydrolysing reaction, the solvent can be determined counting in further reaction steps and the aftertreatment since the presence of a solvent does not affect the reaction.

As to the conversion process of trans-δ-hydroxydihydrochrysanthemic acid to cis-chrysanthemic acid, following methods are known;

i. refluxing trans-δ-hydroxydihydrochrysanthemic acid ester with more than equimolar amount of potassium tertiary-butoxide in benzene to obtain cis-dihydrochrysanthemolactone, and ii. heating the obtained lactone in the presence of pyridine and magnesium bromide, and cleaving the lactone ring to obtain cis-chrysanthemic acid (DT-OS 2010182).

The above-mentioned reaction requires two reaction steps to obtain the aimed cis-chrysanthemic acid from trans-δ-hydroxydihydrochrysanthemic acid ester as a starting material, on the contrary the present reaction can give an objective compound with one step reaction.

The preparation of Step II according to the present invention will be illustrated in greater detail as follows.

As the strong base used for the present process, though the strong base used is converted to the corresponding alkoxide in the reaction medium, alkali metal alkoxide, alkali metal hydride, alkali metal amide and alkali metal may be employed, but not limitative thereto. Preferably sodium methoxide and sodium ethoxide are illustrated as they are cheaply obtainable.

And the presence of a solvent is not essential, but the reaction will proceed smoothly if present.

Examples of the solvent used in Step II, that is, inert solvent not reacted with alkali metal alkoxide, are exemplified by the hydrocarbon solvent (e.g. toluene, xylene, cumene, liquid paraffin), the chlorinated hydrocarbon solvent (e.g. monochlorobenzene, dichlorobenzene), amino type solvent (e.g. pyridine, collidine, dimethylaniline, quinoline), the polar solvent (e.g. hexamethyl phosphoric triamide, dimethylsulfoxide, dimethylformamide), the alcohol having high boiling point (e.g. benzyl alcohol, ethylene glycohol), the ether having high boiling point (e.g. diethyleneglycohol dimethyl ether), and the mixture thereof.

The reaction can be carried out below the temperature of 250° C, preferably at the range between 100° C and 200° C. And the reaction may be carried out under increased pressure to operate the desired reaction temperature.

Thus obtained mixture of cis-chrysanthemic acid and iso-cis-chrysanthemic acid is treated with a mineral acid or an organic acid in the presence or absence of an organic solvent to convert selectively iso-cis-chrysanthemic acid to cis-dihydrochrysanthemolactone. Cis-chrysanthemic acid is obtained by separating the resultant mixture to acid part and neutral part by addition of caustic alkali, and removing the lactone included in the neutral part by an ordinary method.

Examples of the solvents used in the reaction are exemplified by the hydrocarbon solvent (e.g. hexane, toluene), the halogenated hydrocarbon solvent (e.g. chloroform, dichloroethane), the ether type solvent (e.g. ethyl ether, tetrahydrofuran), the ester type solvent (e.g. ethyl acetate), the organic acid type solvent (e.g. acetic acid) and ketone type solvent (e.g. acetone). The presence of a solvent is not essential, but preferable.

Water may be used as a solvent to increase selectivity of the reaction.

Examples of the acid catalysts include the mineral acid (e.g. dilute sulfuric acid, dilute hydrochloric acid), and the organic acid (e.g. para-toluenesulfonic acid, oxalic acid maleic acid; trichloroacetic acid, dichloroacetic acid), preferably oxalic acid and maleic acid are used to increase selectivity of the reaction.

Thus obtained cis-chrysanthemic acid includes a small amount of iso-cis-chrysanthemic acid, but, if necessary, it can be easily purified by recrystallization method or crystallization as a suitable metal salt or an amine salt thereof.

The method of the present invention will be illustrated in detail with reference to the following examples, which are not intended to limit the scope of the present invention.

REFERENCE EXAMPLE 1

2 g of (±)-trans-chrysanthemic acid was mixed with 100 ml of 5% (w/w) aqueous solution of sulfuric acid, and 0.3 g of sodium lauryl sulfate was added to the resultant mixture. Then, the mixture was refluxed with stirring for 3 hours and a half.

After cooling, petroleum ether was added to the mixture and the organic layer was separated. The aqueous layer was extracted with petroleum ether further two times. Petroleum ether extracts were combined, washed with saturated sodium chloride aqueous solution and dried over sodium sulfate. The solvent was evaporated to recover 0.7 g of intact (±)-trans-chrysanthemic acid.

The above-mentioned aqueous layer was saturated with sodium chloride and extracted with ethyl ether three times. Combined ether extracts were combined and washed with saturated sodium chloride aqueous solution. After drying over sodium sulfate, the solvent was evaporated to obtain 1.4 g of trans-δ-hydroxydihydrochrysanthemic acid as white crystals.

REFERENCE EXAMPLE 2

3.5 g of (±)-trans-δ-hydroxydihydrochrysanthemic acid was mixed with 100 ml of 5% (w/w) aqueous solution of sulfuric acid and 0.3 g of sodium lauryl sulfate was added to the resultant mixture.

The mixture was treated as Reference example 1. From petroleum ether extracts, 1.6 g of (±)-trans-chrysanthemic acid, and from ether extracts 1.4 g of (±)-trans-δ-hydroxydihydrochrysanthemic acid were obtained respectively.

Gas-liquid layer chromatographical analysis showed that there existed 1–2% by weight of (±)-iso-trans-chrysanthemic acid in (±)-trans-chrysanthemic acid part.

manner, made into mosquito coils containing 0.3% and 0.6% of each compound, respectively.

Test method A

About 20 Northern house mosquito adults (*Culex Pipens pullens*) per group were liberated in a $(70\ cm)^3$ glass chamber. 1 Gram of each of the thus prepared mosquito coils was ignited at the both ends and each of ignited coils was placed at the center of the respective chambers. The number of knocked down mosquitoes was counted with the lapse of time for 24 minutes. This procedure was repeated several times to calculate $KT_{50}$ value (the same as mentioned above). The results are given in Table 1.

Test method B 0.8 Gram of each of mosquito coils was ignited at the both ends and placed in a $(6\ feet)^3$ Peet Grady chamber in which an electric fan was set and started. After the mosquito coil was burned out, the fan was removed, about 50 Northern house mosquito adults were liberated therein and the number of knocked down mosquitoes was counted with the lapse of time for 2 hours to calculate $KT_{50}$ value (the same as mentioned above). The number of dead mosquitoes was counted on the next day to calculate the mortality. The results are shown in Table 1.

Table 1

| Compound tested | Concentration (%) | Test method A $KT_{50}$ (min., sec.) | Test Method B | | | | | | | $KT_{50}$ (min.) | Mortality (%) |
| --- | --- | --- | --- | --- | --- | --- | --- | --- | --- | --- | --- |
| | | | Knock-down (%) with the lapse of time | | | | | | | | |
| | | | 5' | 10' | 20' | 40' | 60' | 90' | 120' | | |
| 3-Phenoxybenzyl (+)-cis-chrysanthemate | 0.3 | 15'30" | 1 | 6 | 48 | 64 | 88 | 88 | 90 | 22.5' | 23 |
| | 0.6 | 11'00" | 14 | 49 | 65 | 84 | 92 | 95 | 96 | 10.5' | 54 |
| 3-Phenoxybenzyl (+)-trans-chrysanthemate | 0.3 | 19'30" | 0 | 0 | 10 | 29 | 58 | 76 | 77 | 54' | 12 |
| | 0.6 | 17'00" | 1 | 4 | 25 | 54 | 76 | 82 | 88 | 36.2' | 20 |
| Allethrin | 0.3 | 14'30" | 7 | 27 | 34 | 41 | 36 | 30 | 24 | >120' | 5 |
| | 0.6 | 10'30" | 20 | 42 | 55 | 68 | 64 | 57 | 53 | 15.2' | 9 |

REFERENCE EXAMPLE 3

10 g of (±)-trans-chrysanthemic acid was treated as Reference example 1 with the same conditions, except for prolonging the reflux time to 5 hours and a half. 8.3 g of (±)-trans-chrysanthemic acid and 1.5 g of (±)-trans-δ-hydroxydihydrochrysanthemic acid were obtained.

REFERENCE EXAMPLE 4

4 g of (±)-trans-δ-chlorodihydrochrysanthemic acid, 3.13 g of sodium hydroxide and 60 ml of water were mixed. The resulting solution was warmed to 60° C for 2 hours with stirring. Small quantity of solution was picked up and acidified under cooling and extracted with ether.

The extract was analyzed by gas-liquid layer chromatography after esterified with diazomethane. It showed that only slight quantity of (±)-trans-δ-hydroxydihydrochrysanthemic acid was formed and the mains were (±)-trans-chrysanthemic acid, which were formed by removing hydrogen chloride, and intact (±)-trans-δ-chlorodihydrochrysanthemic acid.

REFERENCE EXAMPLE 5

A given amount of each of 3-phenoxybenzyl (±)-cis-chrysanthemate, 3-phenoxybenzyl (±)-trans-chrysanthemate and commercial allethrin was, in the ordinary

STEP 1

EXAMPLE 1

8.4 g of (±)-trans-chrysanthemic acid was dissolved in 20 g of toluene. 15 g of concentrated hydrochloric aqueous solution was added to the resultant solution, then warmed to 50°–55° C and maintained for 2 hours with stirring and blowing hydrogen chloride gas through the solution continuously. After cooling, water was added to remove hydrogen chloride to aqueous layer. To the separated toluene layer were added 100 ml of water and 5 g of calcium carbonate, and the mixture was warmed to 50°–60° C for 1 hour with stirring. After unreacted calcium carbonate was filtered off toluene layer was evaporated to obtain 1.7 g of (±)-trans-chrysanthemic acid. The aqueous layer was acidified with dilute aqueous hydrochloric acid solution and extracted with ether 3 times. Ether extracts were dried and evaporated to obtain 6.3 g of (±)-trans-δ-hydroxydihydrochrysanthemic acid as white crystals.

EXAMPLE 2

15 g (±)-trans-chrysanthemic acid was dissolved in anhydrous ethyl alcohol and cooled to −5° – −10° C. At this temperature, the resultant solution was saturated with hydrogen chloride gas, and then 11.8 g of thionyl chloride was added dropwise thereto. The temperature was raised gradually to the room temperature and the solution was allowed to stand at room temperature overnight. 500 ml of water was added thereto and the mixture was extracted with ether 3 times. Ether extracts were washed with 5% aqueous solution of sodium hydroxide and dried over anhydrous sodium sulfate and evaporated to give 17.2 g of (±)-trans-δ-chlorodihydrochrysanthemic acid as oil. After the alkali aqueous layer was acidified with dilute hydrochloric acid, the solution was extracted with ether. Ether extract was dried and evaporated to obtain 1.8 g of (±)-trans-hydroxydihydrochrysanthemic acid.

Above mentioned oil, 100 ml of water and 8 g of calcium carbonate were mixed and then the mixture was warmed to 60°–70° C and stirred for 4 hours. After excess calcium carbonate was filtered off, the mixture was extracted with ether 2 times. Ether extracts were dried and evaporated to afford 15.3 g of oil. The oil contained 63.5% by weight of (±)-trans-hydroxydihydrochrysanthemic acid and 26.5% by weight of (±)-trans-chrysanthemic acid by gas-liquid phase chromatographical analysis after esterification with diazomethane.

EXAMPLE 3

8.4 g of (±)-trans-chrysanthemic acid was treated as in the same way as in Example 1, except for changing calcium carbonate to magnesium carbonate. 1.8 g of (±)-trans-chrysanthemic acid and 6.4 g of (±)-trans-δ-hydroxydihydrochrysanthemic acid were obtained respectively.

STEP 2

EXAMPLE 4

6.0 g of (±)-trans-δ-hydroxydihydrochrysanthemic acid methyl ester and 100 ml of dry benzene were charged to the 200 ml flask. To make the whole completely dry, benzene was refluxed to circulate the column packed with sodium hydroxide pellet for 1 hour and a half. Then, 1.94 g of sodium methoxide and 100 ml of xylene were added dropwise thereto and the resultant solution was heated to the boiling point of xylene to remove benzene as distillate, and then maintained at the same temperature for 3 hours under refluxing condition.

After cooling, excess aqueous dilute hydrochloric acid was added thereto and the organic layer was separated. The organic layer was extracted with 5% aqueous solution of sodium hydroxide. The organic layer was evaporated to obtain 2.70 g of (±)-dihydrochrysanthemolactone. The alkaline aqueous layer was acidified with dilute aqueous hydrochloric acid and then extracted with ether. After being dried, the ether extracts were evaporated to obtain 1.90 g of acidic material.

Thus obtained acid material consisted of 90% by weight of (±)-iso-cis-chrysanthemic acid and 10% by weight of (±)-cis-chrysanthemic acid, as shown by gas-liuid phase chromatographical analysis.

EXAMPLE 5

10.0 g of (±)-trans-δ-hydroxydihydrochrysanthemic acid methyl ester was treated as in the same way as Example 4, except for changing the amount of sodium methoxide to 3.23 g and the reaction temperature to 160°–170° C. 6.17 g of acid material was obtained and it contained the nearly same amount of (±)-cis-chrysanthemic acid and (±)-iso-cis-chrysanthemic acid.

EXAMPLE 6

6.0 g of (±)-trans-δ-hydroxydihydrochrysanthemic acid methyl ester was treated as in the same way as Example 4, except for using 1.94 g of sodium methoxide and 10 ml of hexamethyl phosphorus triamide. 2.91 g of acid material was obtained and it contained about 80% by weight of (±)-iso-cis-chrysanthemic acid and 20% by weight of (±)-cis-chrysanthemic acid. From the neutral part 1.5 g of (±)-dihydrochrysanthemolactone was obtained.

EXAMPLE 7

10.0 g of (±)-trans-δ-hydroxydihydrochrysanthemic acid methyl ester was treated as in the same way as Example 4, except for changing the amount of sodium methoxide to 3.23 g and using 13.50 g of benzyl alcohol in place of xylene and maintaining the reaction temperature to 165°–175° C for 3 hours.

7.8 g of acid material was obtained and it contained the nearly same amount of (±)-cis-chrysanthemic acid and (±)-iso-cis-chrysanthemic acid.

STEP 3

EXAMPLE 8

5 g of the mixture of (±)-cis-chrysanthemic acid and (±)-iso-cis-chrysanthemic acid (ratio of cis : iso-cis was 55 : 45), 50 ml of water and 0.25 g of maleic acid were mixed and refluxed with stirring for 5 hours. The reaction mixture was cooled and extracted with ether 3 times. The ether extracts were separated to acid material and neutral material by washing with 5% of aqueous solution of sodium hydroxide. The aqueous solution was acidified with dilute hydrochloric acid and extracted with ether three times. Ether extracts were dried and evaporated to obtain 2.1 g of acid material. This acid material contained 90% by weight of (±)-cis-chrysanthemic acid and 10% by weight of (±)-iso-cis-chrysanthemic acid. Recrystallization from n-hexane-ether afforded 1.8 g of (±)-cis-chrysanthemic acid (which were contaminated with 2% by weight of (±)-iso-cis-chrysanthemic acid). The above-mentioned ether layer was dried and evaporated to obtain 2.00 g of (±)-dihydrochrysanthemolactone.

EXAMPLE 9

5.0 g of the mixture (the same material used in Example 8) was treated in the same way as in Example 8, except for replacing 0.25 g of maleic acid by 0.25 g of oxalic acid and refluxing the reaction mixture for 2 hours, to obtain 2.6 g of cis-chrysanthemic acid (containing 6% by weight of iso-cis-chrysanthemic acid) and 1.8 g of cis-dihydrochrysanthemolactone.

What is claimed is:
1. A process for preparing cis-chrysanthemic acid of the formula (I)

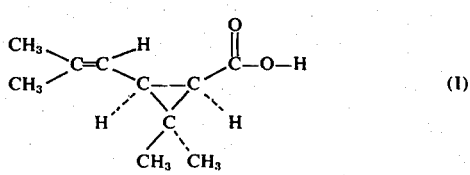

(I)

which comprises preparing a trans-δ-hydroxydihydrochrysanthemic acid ester of the formula (V)

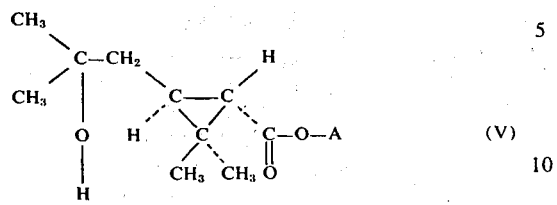

(V)

wherein A represents C₁–C₄ alkyl or benzyl
by either hydrolyzing an ester of trans-δ-halogenodihydrochrysanthemic acid of the formula (VI)

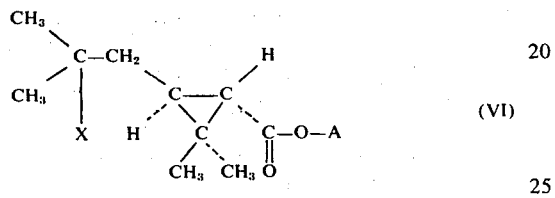

(VI)

wherein X is a halogen atom under neutral conditions maintained by the presence of calcium carbonate or magnesium carbonate or
by hydrolyzing a trans-δ-halogenodihydrochrysanthemic acid of the formula (VIII)

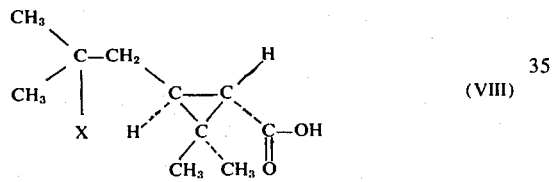

(VIII)

wherein X is a halogen atom under neutral conditions maintained by the presence of calcium carbonate or magnesium carbonate with further esterifying said hydrolyzed acid with an alcohol of the formula A-OH wherein A is defined above in the presence of a mineral acid at about room temperature,
reacting said trans-δ-hydroxydihydrochrysanthemic acid ester of the formula (V) with more than an equimolar amount of a strong base selected from the group consisting of alkali metal alkoxide, alkali metal hydride, alkali metal amide and alkali metal in the presence or absence of an inert solvent at a temperature ranging from 100° C to 200° C to prepare a mixture of cis-chrysanthemic acid of the formula (I) and iso-cis-chrysanthemic acid of the formula (III)

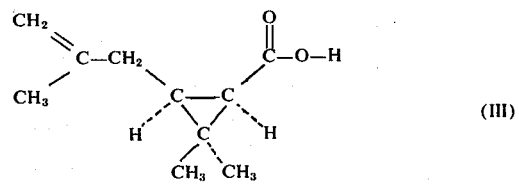

(III)

treating said mixture with water in the presence of an acid catalyst, in the presence or absence of an inert solvent to convert iso-cis-chrysanthemic acid of the formula (III) selectively to cis-dihydrochrysanthemolactone of the formula (II)

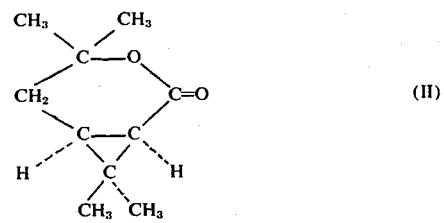

(II)

and separating the acid part from the neutral part by adding an aqueous alkaline agent to the resulting mixture and removing the lactone of the formula (II) as the neutral part according to an ordinary method.

* * * * *